| United States Patent [19] | [11] Patent Number: 4,565,722 |
|---|---|
| Highgate et al. | [45] Date of Patent: Jan. 21, 1986 |

[54] DEFORMABLE POLYMERIC COMPOSITIONS

[76] Inventors: Donald J. Highgate; John D. Frankland, both of IH Laboratories Limited, Meopham Trading Estate, Meopham, Gravesend, Kent, United Kingdom, DA13 OLT

[21] Appl. No.: 607,689

[22] Filed: May 7, 1984

[30] Foreign Application Priority Data

May 9, 1983 [GB] United Kingdom ............... 8312728
Feb. 29, 1984 [GB] United Kingdom ............... 8405258

[51] Int. Cl.⁴ .................. A61F 13/00; A61C 5/04
[52] U.S. Cl. ............................ 428/36; 428/913; 604/358; 604/385 R; 433/226
[58] Field of Search ............. 428/36, 913; 525/937; 3/36; 604/281, 256, 385; 217/110; 264/2.6, 2.7, 289.6, 321, 343, 342 R, DIG. 71, 288.8, 289.3; 174/DIG. 8; 114/228; 521/905; 433/226, 228, 201; 523/116

[56] References Cited

U.S. PATENT DOCUMENTS

| 3,018,778 | 1/1962 | Brilliant | 128/269 |
| 3,306,966 | 2/1967 | Matejcek et al. | 264/321 |
| 3,663,678 | 5/1972 | Miller | 264/230 |
| 4,096,230 | 6/1978 | Haerr | 264/321 |
| 4,157,085 | 6/1979 | Austad | 128/1 R |

FOREIGN PATENT DOCUMENTS 1566552 5/1980 United Kingdom .

*Primary Examiner*—John E. Kittle
*Assistant Examiner*—Thomas Saitta
*Attorney, Agent, or Firm*—Price, Heneveld, Huizenga & Cooper

[57] ABSTRACT

A shaped polymeric composition, for surgical or dental use, can absorb liquid and thereby expand or contract in one direction, substantially without similar expansion or contraction in another direction. Embodiments of the invention are breast implants, tapered dental inserts, and tubular bodies for use as nerve approximation sheaths.

5 Claims, 10 Drawing Figures

DEFORMABLE POLYMERIC COMPOSITIONS

A water-swellable polymer swells when it absorbs water and, likewise, an oil-swellable polymer swells when it absorbs oil. A shaped composition of such a polymer will undergo an increase in one dimension substantially the same as the increase (expressed as a percentage) in every other dimension unless the shaped composition is physically restrained. For instance, if the composition is formed as a tubular sheath, the thickness of the sheath will increase both inwardly and outwardly, i.e. the internal and external diameters become respectively less and greater, and the length of the sheath will increase. Increase of the external diameter can be prevented by restraining the outside of the sheath by a non-extensible material. If the shaped composition is a tapered plug, the plug will swell both axially and radially.

GB-A-1566552 describes articles such as sleeves and tubes, for uses such as marine engineering. Such an article is made by forming a first article having first dimensions and deforming this by heat and pressure, but without melting, to the desired final article having second dimensions, and cooling the final article, in which the final article is formed of a polymer which can absorb a liquid and which, upon absorbing the liquid with substantially no change in temperature, will change its dimensions substantially to or towards the different, first, dimensions. Thus the first article is deformed without melting and is then restored to its original dimensions, or to near its original dimensions, as a result of absorbing the liquid. Deformation that occurs upon absorbing the liquid may involve either swelling or shrinking.

It is also known to make polymeric articles which can be caused to shrink and/or change shape as a result of heating, but it is sometimes impracticable to effect the necessary heating.

Polymeric insert plugs and sheaths for dental and surgical uses are known, but they have generally incurred serious disadvantages. For instance, it is known to provide a large range of differently-sized insert points of rubber and to shape a dental cavity to receive one of these inserts. It is inconvenient to have to store a large number of sizes of inserts, their fitting requires high precision drilling, since the insert and cavity must be the same size, and the inserts may lack strength.

The use of a simple hydrophilic polymer, e.g. as a dental insert, is unsatisfactory since it must be provided in a form whose dimension along the axis of insertion is much greater than its radial dimension; if it is possible to shape it so that it swells radially sufficiently to be fixed in the cavity but insufficiently to fracture the tooth, it will swell axially to a degree that it lifts the normal surface cosmetic filling off the tooth. It has been proposed to provide inserts by curing a hydrophilic polymer in situ in the cavity. However, curable material may escape in small quantities from the cavity, before curing, and excess cross-linking agent and/or initiator may escape even during subsequent use. Both these possibilities are very undesirable. Further, such polymers have proved to be unsatisfactory for prolonged use and to incur the substantial risk of fracturing the tooth.

Breast reconstruction following surgery or accident is an essential psychological service for many patients, and external devices for this purpose, and internal breast implants, are known. Permanent implants are normally suitably-shaped silicon rubber devices, but a device of the desired size cannot normally be implanted directly because the skin and muscle structure is not extensive enough to accommodate an implant of realistic size. In order to avoid this problem, a so-called "serial expansion implant" has been employed. This consists of a balloon which is embedded beneath the skin and which is inflated (using saline solution) in a series of stages over a total period of 4 to 6 weeks. The effect of this treatment is to stretch the overlying tissue gently, and to allow for the subsequent insertion of a permanent implant of full size. The treatment is effective, but involves two separate surgical procedures and requires the patient to make an extensive series of outpatient visits, for inflation of the serial expansion device.

It has been our object to avoid these disadvantages and to provide shaped compositions which are useful for surgical or dental uses in the human or animal body.

According to the present invention, a shaped polymeric composition for surgical or dental use is capable of absorbing liquid and, upon absorbing the liquid, expands or contracts in one direction without similar expansion or contraction in another direction. Thus, the shaped composition does not expand or contract isotropically or uniformly (as a percentage of its initial dimensions) in every direction but, instead, has different expansion or contraction properties in different directions.

One example of a shaped composition of the invention is a cylindrical insert, e.g. for use as a breast implant, which may expand in the axial direction while its diameter remains substantially unchanged. Another example of the invention is a tapered insert plug, which may expand in all radial directions while its axial length remains substantially unchanged. A further example is a tubular sheath which may expand inwardly (so as to reduce its internal diameter) without expanding outwardly, i.e. without any increase in its outer diameter, and generally also without expanding axially.

The shaped composition will normally have strain fixed into it in at least one direction, but not generally in all directions, and this strain is released upon absorbing the aqueous liquid (generally with little or no change in temperature) so as to cause a tendency to shrink in that direction, generally in opposition to the normal tendency to swell. The shaped composition may be made, for example, by heating the composition in air or oil (without melting, e.g. in air at 150°–160° C.), applying pressure, strain or tension, and cooling. A hydraulic press or "shaped forces" may be used. For sensitive materials, or where large changes in dimensions are required, it may be preferable to allow the composition to absorb liquid, deform the swollen material at ambient conditions and then remove liquid. Again, partial swelling and heating may be used. In each case, the strain is fixed in by cooling/removing liquid.

The polymeric composition is preferably hydrophilic. The liquid which is absorbed into it to cause a change in dimensions may be an aqueous liquid or a polar organic liquid, for instance a monohydroxy or polyhydroxy, e.g. dihydroxy, alcohol. The aqueous liquid may be water but part at least of the aqueous liquid is generally a body fluid, for instance saliva or blood.

The extent to which the shaped composition changes its dimensions may depend upon the amount of liquid absorbed into it. A dimension may increase by a factor of up to 5. Sometimes, there is a threshold amount below which there is little or no significant change in dimensions. It is often convenient to absorb into the composition, while outside the body, a polar liquid such as glycerol and/or water in an amount such that the shaped composition will change its dimensions upon absorbing only a very small additional amount of added or body liquid. This is advantageous as it ensures that the critical dimension change that is required for surgical or dental uses may occur quickly after fitting the shaped composition in the body.

Reference should be made to GB-A-1566552 for a full discussion of suitable hydrophilic polymers and suitable ways of deforming articles formed from them by heat and pressure to form the desired shaped compositions which will undergo change in dimensions upon absorbing body liquids or other suitable polar liquids. The composition is best based primarily or solely on a copolymer of N-vinyl-2-pyrrolidone with one or more hydrophilic or hydrophobic ethylenically-unsaturated comonomers, such as those discussed in GB-A-1566552. The amount of N-vinyl-2-pyrrolidone in the copolymer is generally between 10 and 80% (by weight of copolymerisable monomers). The amount of hydrophobic monomers is generally from 20 to 80% by weight. If the comonomers include highly hydrophilic monomers such as allyloxysilane, the total amount of hydrophilic monomers, including N-vinyl-2-pyrrolidone, may be less than 30%, but otherwise the total amount of hydrophilic monomers is often from 40 to 80%, by weight.

Particularly preferred polymeric compositions are formed from 20 to 80%, generally 25 to 70%, by weight N-vinyl-2-pyrrolidone with the balance being provided by hydrophobic monomers such as acrylonitrile or alkyl (generally methyl or butyl) acrylate or methacrylate. One preferred polymer is a copolymer of 30 to 70%, and generally about 50%, by weight N-vinyl-2-pyrrolidone with the balance of acrylonitrile, while other preferred copolymers are formed from 20 to 80% by weight N-vinyl-2-pyrrolidone, and the balance being one or both of methyl and butyl methacrylates.

As mentioned in GB-A-1566552, the polymers are preferably cross-linked, for instance by the use of 0.2 to 2% by weight allyl methacrylate or another appropriate cross-linking agent.

Other hydrophilic monomers which can advantageously be copolymerised with the vinyl pyrrolidone include hydroxyalkyl acrylates and methacrylates and sulphonated monomers. The use of silanes is particularly advantageous for dental inserts and other shaped compositions which are to be bonded in position to a silicone gel base.

Antiseptic components such as formaldehyde may be included in the composition when initially manufactured, or they may be added before or after deformation of the initial article to the shaped composition.

The composition which is to be subjected to strain may be formed by polymerising the polymerisable mixture of monomers or prepolymers in a mould having the intended final dimensions, or it may be made by machining, heat-welding or cutting from a mass of the composition. It is then deformed to produce and fix the desired internal strain and to produce the shaped composition of the desired initial dimensions, ready for use in the body.

In order that a, say, dental insert can swell without the risk of shattering the surrounding tooth, it may be desirable to include in the polymeric composition bubbles of vapour, e.g. of a low molecular weight alcohol, which condense at body temperature when the pressure increases undesirably, for instance to from 150 to 500 kPa. If the polymer expands more than is necessary to form a tight fit, the vapour condenses and the bubbles collapse.

A shaped polymeric composition of the invention may be formulated in order that it has desired physical properties in addition to its deformation on the absorption of liquid. For example, the composition of a sheath, e.g. for use as a nerve approximation sheath, is preferably transparent, while the composition of a dental insert preferably includes a material such as barium sulphate which is opaque to X-rays.

The invention will now be illustrated, by way of example only, with reference to the accompanying drawings, in which FIGS. 1, 3, 5 and 9 illustrate embodiments of the invention. In particular:

Figure 5:
Figure 6:
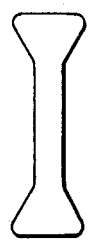
Figure 7:
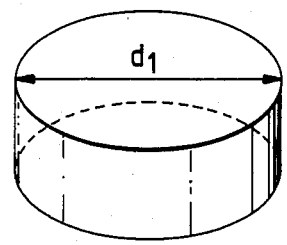
Figure 8:
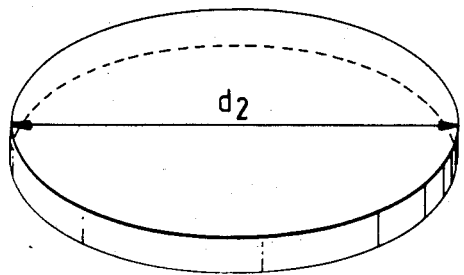
Figure 9:
Figure 10:
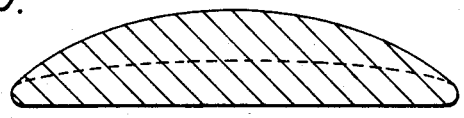

FIGS. 5 and 6 are side views of a plug for blocking a body passage and having, respectively, initial and final dimensions; and FIGS. 7 and 8 are plan views of blanks from which may be prepared the essentially cylindrical insert whose initial and final dimensions, respectively, are shown in FIGS. 9 and 10.

Figure 1:
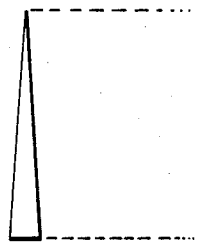
FIGS. 1 and 2 are side views of a tapered dental insert with, respectively, initial and final dimensions.
Figure 2:
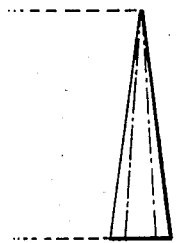

FIG. 1 shows a typical shape for a polymeric composition, for surgical or dental use, in the form of an insert having axial and transverse dimensions, which will absorb a body liquid or other polar liquid and which, upon absorbing this liquid, expands in a transverse direction substantially without expansion in its axial direction (as shown in FIG. 2). The product may initially be made by forming a rod of the desired polymeric material, hydrating this by impregnation with water or other suitable liquid, stretching it while hydrated, drying it while permitting either no axial shrinkage or only controlled axial shrinkage, and cutting it to shape, e.g. to form the product of FIG. 1.

When this insert is inserted in a body cavity, or is in some other way brought into contact with an appropriate liquid, absorption of liquid will cause swelling in all directions but will also release axial strain set into the product during manufacture and so there will be axial shrinkage. By appropriate choice of the stretching conditions during manufacture, the axial shrinkage can be selected to be equivalent to the axial swelling that will occur, so that the axial length stays unchanged while the product swells radially. Typically, the ratio of the radius when swollen to the radius before swelling is from 1.1:1 to 6.1:1, and generally from 1.1:1 to 1.3:1; if the product is stretched by a similar ratio during manufacture, the resultant product will swell radially but not axially.

A tapered insert of the type illustrated in FIG. 1 is of particular value as an endodontic point for insertion into a tooth after the nerve cavity has been removed. Since it does not expand axially, it does not load the final cosmetic surface applied to the outer surface of the cavity and, since it expands laterally, it is possible to achieve a good fit by selection out of a relatively small number of inserts, instead of the very large number which is necessary when using rubber inserts. Further, it will fill irregularities in the nerve channel, and so the channel does not have to be prepared so accurately as for a rubber insert. The insert can be of very high strength, thus facilitating removal if this becomes necessary.

Figure 3:
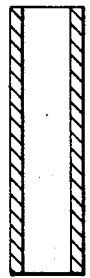
FIGS. 3 and 4 are cross-sections through a tubular article having, respectively, initial and final dimensions.
Figure 4:
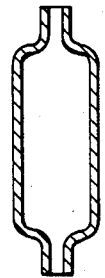

FIG. 3 illustrates a composition which is in the form of a sheath, which will absorb a liquid and which, upon absorbing the liquid while unconstrained, will shrink internally along part or all of its length without external expansion along that part of its length or along all of its length. Thus a sheath as shown in FIG. 4 may be formed by conventional techniques from hydrated polymer, radially expanded on a mandrel to form a sheath as shown in FIG. 3 and then dried in this configuration, and then brought into contact with body liquid or other appropriate liquids. Such a sheath is of particular value as a nerve approximation sheath for holding severed nerve ends into close proximity. The severed ends are inserted into the sheath while it has the shape shown in FIG. 3; on liquid absorption, it will deform to the shape shown in FIG. 4, so that the contracted ends of the sheath provide a soft and pliable grip on the nerves. Similarly, the sheath can be made on a larger scale for holding veins or arteries, or even bones, during healing.

Inserts according to the invention can be used for blocking passages within the body. For instance, in insert shown in FIG. 5, which will swell in contact with body liquid to a shape shown in FIG. 6, can be used for providing a permanent but non-irritant Fallopian tube closure.

FIG. 7 illustrates a cylindrical blank of diameter $d_1$. This blank is subjected to pressure to give a prestressed blank of diameter $d_2$, as shown in FIG. 8. The breast implant shown in cross-section in FIG. 9, again having diameter $d_2$, is cut from the second blank (whose outline is shown, for reference). On hydration, the insert expands in thickness only provided that $d_1/d_2$ equals the linear expansion ratio of the material during hydration, to give the expanded insert shown in cross-section in FIG. 10 (which also shows, for reference, the outline of the body of FIG. 9). Such an implant may be coated, if desired, with a porous biocompatible material such a silicone or PTFE, in order to regulate the rate of water uptake, and thereby to control the rate of expansion of the implant and avoid any damage to adjacent tissue by dehydration (by competition for available water with the hydrophilic implant). The rate of hydration may also be controlled by choice of the type and properties of the hydrophilic material which is used for the implant.

We claim:

1. An article for surgical or dental use, said article being of a polymeric composition and specifically shaped for its particular use and capable of water absorption in situ, said article having been prepared by straining in at least one direction while swollen with absorbed water and the straining permanently fixed by removal of the absorbed water whereby upon placement in a body cavity and subsequent exposure to water the dimensions of the article will change in a predetermined and controlled manner as to amount and only in a direction different from that in which it was strained.

2. The article described in claim 1 wherein the article is generally tubular in shape and the water caused controlled dimensional change after placement in a body cavity will be expansion along its axis substantially without radial expansion.

3. The article described in claim 1 wherein the article is generally conical in shape and the water caused controlled dimensional change after placement in a body cavity will be radial expansion substantially without axial expansion.

4. The article as described in claim 1 having trapped therein bubbles of a vapor which will condense at body temperature when subjected to a pressure of 150 to 500 kPa.

5. The article described in claim 1 for surgical use having a generally circular disc-like shape with one surface being convex in its strain fixed condition and the water caused controlled dimensional change will be an increase in convexity of said one surface substantially without radial expansion.

* * * * *